United States Patent [19]

Carter

[11] Patent Number: 5,288,285
[45] Date of Patent: Feb. 22, 1994

[54] HOLDER FOR FILLING SYRINGE WITH RADIOACTIVE LIQUID

[76] Inventor: Wade P. Carter, 1710 Dayton Dr., Lemon Grove, Calif. 91945

[21] Appl. No.: 18,291

[22] Filed: Feb. 16, 1993

[51] Int. Cl.⁵ ............................................. A61N 5/00
[52] U.S. Cl. ......................................... 600/5; 600/4; 604/187; 604/195; 604/199; 604/218
[58] Field of Search ............... 604/187, 218, 117, 199, 604/208, 195, 183; 600/4-7; 141/27, 97

[56] References Cited

U.S. PATENT DOCUMENTS

| | | | |
|---|---|---|---|
| 2,074,401 | 3/1937 | Kauzal | 604/208 X |
| 2,571,302 | 10/1951 | Smith | 141/27 X |
| 2,627,857 | 2/1953 | Marcelli | |
| 3,656,351 | 4/1972 | Raczak | 141/27 X |
| 3,993,063 | 11/1976 | Larrabee | |
| 4,033,346 | 7/1977 | Phillips et al. | 604/208 |
| 4,316,558 | 2/1982 | Kubiak | 222/181 |
| 4,393,864 | 7/1983 | Galkin | |
| 4,401,108 | 8/1983 | Galkin et al. | 600/5 |
| 4,429,724 | 2/1984 | Dorros et al. | 141/27 |
| 4,518,387 | 5/1985 | Murphy et al. | |
| 4,589,870 | 5/1986 | Citrin et al. | 604/210 |
| 4,594,073 | 6/1986 | Stine | |
| 4,883,101 | 11/1989 | Strong | |
| 5,115,816 | 5/1992 | Lee | |
| 5,179,983 | 1/1993 | Cordner et al. | 141/27 |

FOREIGN PATENT DOCUMENTS 0349042  8/1973  U.S.S.R. .................. 604/183

*Primary Examiner*—C. Fred Rosenbaum
*Assistant Examiner*—Noelle Kent Gring
*Attorney, Agent, or Firm*—Calif Tervo

[57] ABSTRACT

A holding device for a syringe while filling the syringe with radioactive liquid allows the syringe to be held such that a user is not exposed to radioactive rays. The holder generally comprises first and second rigid elongate members joined by a hinge. The first member distal end terminates in a finger flange bracket for receiving and retaining a syringe finger flange. The second member distal end terminates in a thumb flange bracket for receiving and retaining a syringe plunger thumb flange. An adjustable metering device restricts the angle through which the arms can move. In an exemplary embodiment, the finger flange and thumb flange brackets are removable.

19 Claims, 2 Drawing Sheets

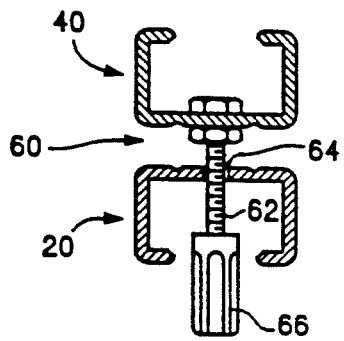
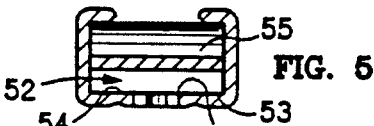
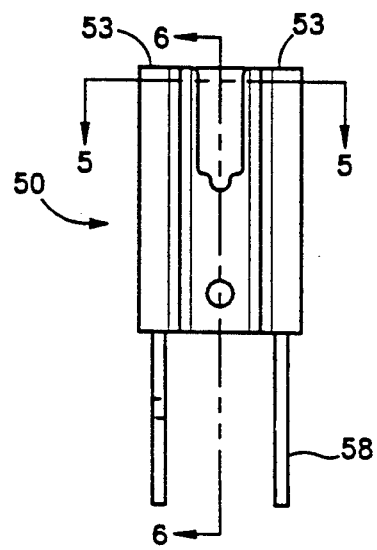
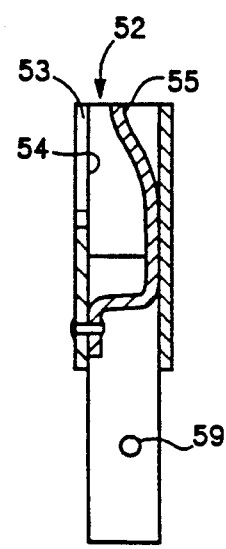
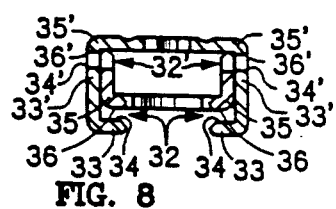
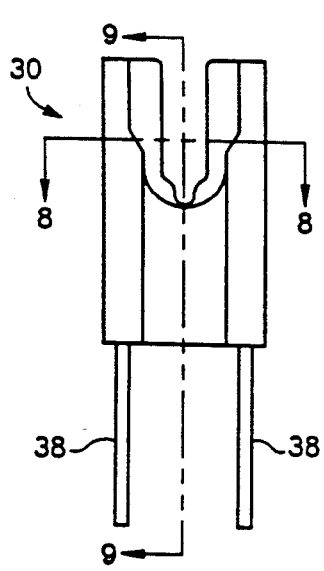
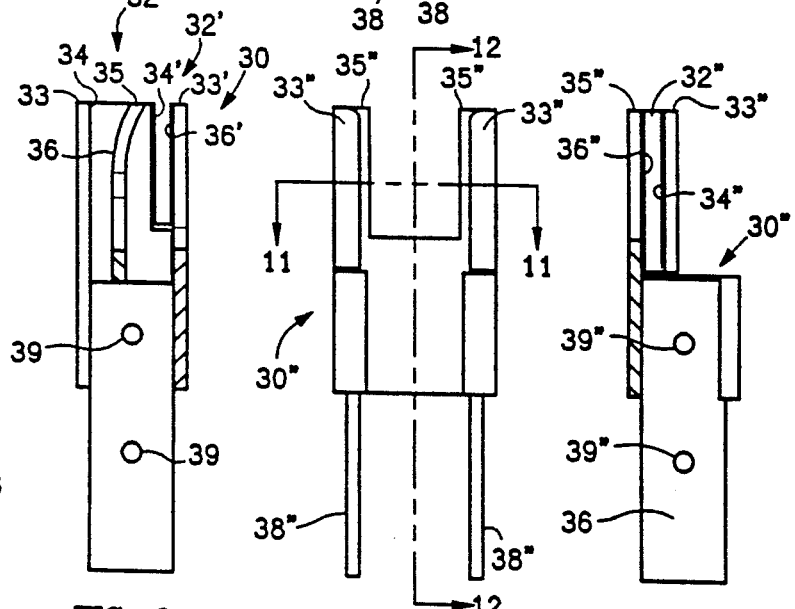

HOLDER FOR FILLING SYRINGE WITH RADIOACTIVE LIQUID

SUMMARY OF THE INVENTION

This invention is a device for holding a syringe while filling the syringe with radioactive liquid. The device allows the syringe to be held such that a user is not exposed to radioactive rays. The holder generally comprises first and second rigid elongate members joined by a hinge.

The first member generally includes a distal arm projecting in a first direction from the hinge and a proximal arm projecting in another direction. The distal arm includes a hinge end connected to the hinge and a distal end terminating in a finger flange bracket for receiving and retaining a syringe finger flange. The finger flange bracket includes a front fork adapted to span the syringe barrel such that the finger flange bears against the back face of the front fork. The finger flange includes a rear fork having a front face. The rear fork is adapted to span the syringe to the back of the finger flange such that the finger flange bears against the rear fork front face. The proximal arm includes a hinge end connected to the hinge and a proximal end.

The second rigid elongate member generally includes a distal arm projecting in a first direction from the hinge and a proximal arm projecting in another direction. The distal arm includes a hinge end connected to the hinge and a distal end terminating in a thumb flange bracket for receiving and retaining a syringe plunger thumb flange. The thumb flange bracket includes a plunger fork having a back face. The plunger fork is adapted to span the plunger such that the thumb flange bears against the fork back face. The proximal arm includes a hinge end connected to the hinge and a proximal end.

The hinge hingedly connects the first member to said second member at the hinge ends such that the first and second members pivot about the hinge from a closed position, wherein the distal ends are in close proximity for receiving the finger flange and the thumb flange of the syringe when the plunger is fully inserted in the barrel and wherein the proximal ends are separated, to an open position, wherein the distal ends are separated, by moving the proximal ends closer together and thereby filling the held syringe.

The arm proximal ends each includes a finger loop to aid in holding and operating the holder. The thumb flange bracket includes a backing plate bearing against the back of said thumb flange.

An adjustable overdraw protection device restricts the angle through which the arms can move.

In an exemplary embodiment, the finger flange and thumb flange brackets are removable.

Other features and many attendant advantages of the invention will become more apparent upon a reading of the following detailed description together with the drawings in which like reference numerals refer to like parts throughout.

BRIEF DESCRIPTION OF THE DRAWINGS

FIG. 3 is a sectional view taken on line 3—3 of FIG. 1 showing the overdraw protection mechanism.

FIG. 4 is a front view of the thumb flange bracket.

FIG. 5 is a sectional view taken on line 5—5 of FIG. 4.

FIG. 6 is a sectional view taken on line 6—6 of FIG. 4 of the thumb flange bracket.

FIG. 7 is a front view of the finger flange bracket of FIG. 1.

FIG. 8 is a sectional view taken on line 8—8 of FIG. 7 of the finger flange bracket.

FIG. 9 is a sectional view taken on line 9—9 of FIG. 7.

FIG. 10 is a front view of an alternate embodiment of the finger flange bracket.

FIG. 11 is a section view taken on line 11—11 of FIG. 10.

FIG. 12 is a section view taken on line 12—12 of FIG. 10.

DETAILED DESCRIPTION OF THE INVENTION

Figure 1:
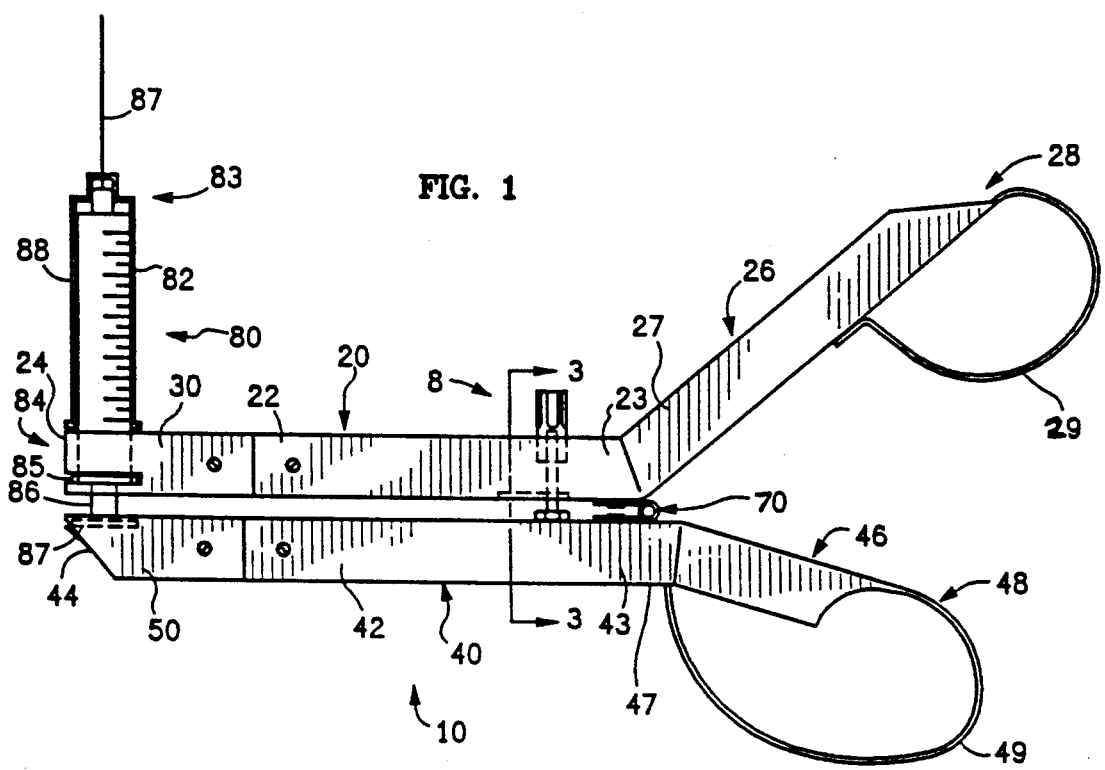
FIG. 1 is a left side view of a preferred embodiment of the holder of the invention in the closed position holding an empty syringe.
Figure 2:
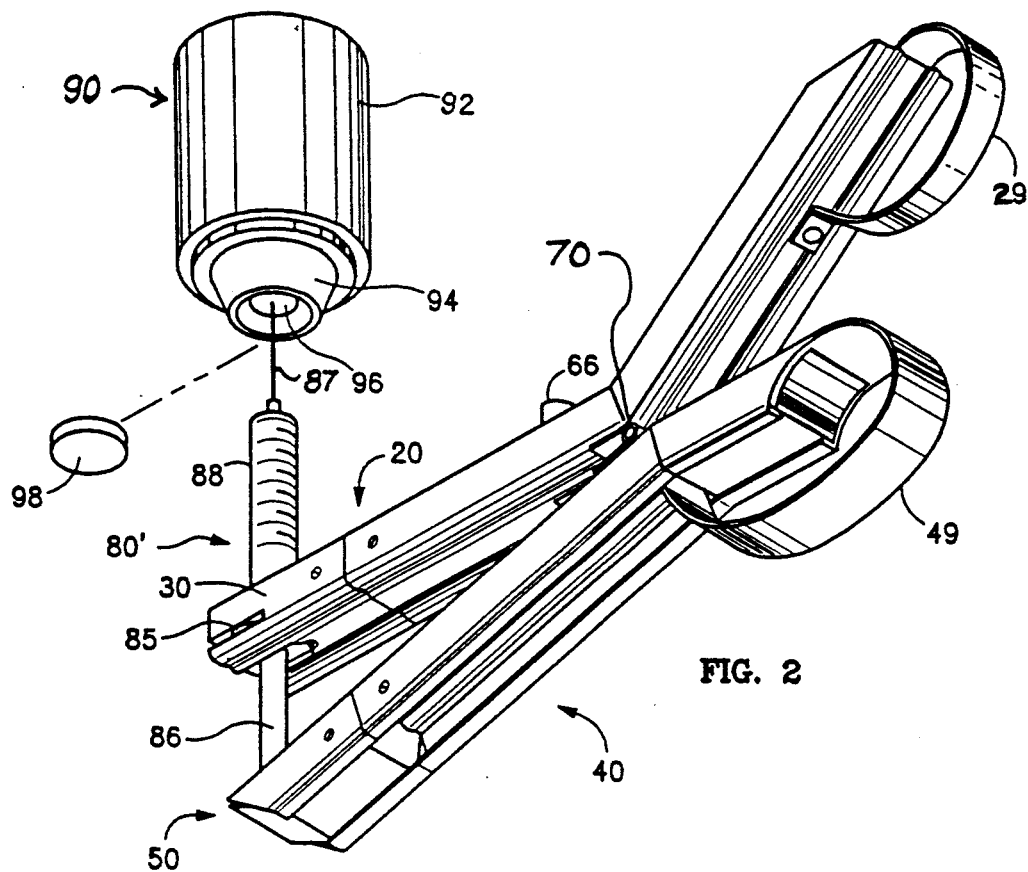
FIG. 2 is a perspective view of holder of FIG. 1 further including a container for radioactive fluid and showing holder in the open position holding a filled syringe.

With reference now to the drawings, and more particularly to FIGS. 1 and 2 thereof, there is shown a preferred embodiment of the holder, denoted generally as 10, of the invention. FIG. 1 is a left side view of a preferred embodiment of the holder 10 of the invention in the closed position holding an empty syringe, denoted generally as 80. FIG. 2 is a perspective view of holder 10 of FIG. 1 further showing a container, pig 90, for holding a vial, not shown, of radioactive fluid and showing holder 10 in the open position holding a filled syringe, denoted generally as 80'.

In hospitals, vials containing radioactive liquids are commonly are kept in pigs 90 that are typically made of shielding material, such as lead. Pig 90 typically includes cylindrical cup 92 having screw lid 94 with opening 96 that is covered by a stopper or gravity lid 98, shown removed, that is easily removed. Removable screw lid 94 retains a vial of radioactive liquid in cup 92 with the vials dispensing end toward opening 96. To access the vial through opening 96, gravity lid 98 is removed.

Syringe 80, of common construction, generally includes barrel 82, plunger 86 and needle 87. Barrel 82 is typically transparent or translucent such that the amount of liquid in the barrel can be seen and includes a front end or needle end 83 and a back end 84. A finger flange 85 on barrel back end 84 has a front side and a back side and is typically held to prevent forward movement of the needle when plunger 86 is pushed forward. Plunger 86 includes a front end that is slidably engaged inside of barrel 82, a central shaft portion and a back end having a thumb flange 87. Thumb flange 87 has a front side toward the barrel and a rear side that is commonly depressed by the user's thumb to push plunger 85 into barrel 82 and thereby eject liquid out of needle 87. FIG. 1 shows an empty syringe 80. Empty syringe 80 is typically characterized in that plunger 86 is inserted as far as it will go into barrel 82. FIG. 2 shows a full syringe 80' characterized by the withdrawal of plunger 86 to the position such that a desired amount of liquid is drawn into barrel 82.

Shield 88 is typically a sleeve that is slipped on barrel 82 from the front and includes a front end for fitting over barrel front end 83 and a back end that terminates in front of finger flange 85. Shield 88 is typically made of shielding material, such as lead, copper or tungsten, that is opaque such that the amount of liquid contained in syringe 80 cannot be seen. Shield 88 may be made of leaded glass such that the amount of liquid in barrel 82 can be seen.

Conventionally, during filling of syringe 80, a hospital worker is exposed to radioactivity emanating from pig opening 96 and from the back of barrel 82.

Holder 10 places the worker's hands off to the side during filling of syringe 80 such that the worker is not exposed to radioactivity escaping from pig opening 96 and back of barrel 82.

Holder 10 generally comprises first rigid elongate member 20 and second rigid elongate member 40 and hinge means, such as hinge 70, hingedly connecting first member 20 to second member 40. First member 20 generally includes a distal arm 22 having a hinge end 23 and a distal end 24 and a proximal arm 26 including a hinge end 27 and a proximal end 28. Second member 40 generally includes distal arm 42 having a hinge end 43 and a distal end 44 and a proximal arm 46 having a hinge end 47 and a proximal end 48. Elongate members 20, 40 preferably are made of strong light-weight material, such as aluminum channel.

Elongate members 20,40 are at all times co-planar and pivot about hinge 70 from the closed position holding empty syringe 80 shown in FIG. 1 to the open position holding full syringe 80' shown in FIG. 2. In the closed position, distal arms 22,42 are substantially parallel to one another and proximal arms 26,46 proceed outward from hinge in a separated condition. First and second members 20,40 are pivoted about hinge 70 to the open position of FIG. 2, wherein distal ends 24,44 are separated, by moving proximal ends 28,48 closer together. Proximate ends 28,48 are adapted for gripping by a single hand and include grip means, such as finger loops 29,49, for facilitating opening and closing of holder 10.

As best seen in FIG. 3, holder 10 includes metering means or adjustable overdraw protection means, denoted generally as 60, for restricting the distance between elongate member distal ends 24,44 in the open position. FIG. 3 is a sectional view taken on line 3—3 of Figure showing the overdraw protection mechanism 60. Overdraw protection means 60 includes threaded rod 62 attached to the distal arm of one elongate member and extending thru orifice 64 in the other member and an adjustment nut 66 threaded thereon which will not pass thru orifice 64. Adjusting nut 66 adjusts the maximum separation distance between distal arm ends 24,44. In this manner a predetermined amount of plunger movement and the corresponding amount of fluid can be drawn. Thus, a holder 10 can be preadjusted to draw a specific amount of fluid. Other adjusting means are contemplated. For example, a similar result is obtainable by using a rod and nut device between proximal arms, wherein the nut is between the arm and will not pass thru the orifice, to adjust the minimum closure distance between proximal ends 28,48.

First member distal arm distal end 24 terminates in finger flange bracket means, such as finger flange bracket 30, for receiving and retaining syringe finger flange 85. Preferably, finger flange bracket 30 is adapted to accommodate a variety of sizes of finger flanges. A preferred embodiment of such a finger flange 30 is shown in FIGS. 7, 8 and 9. FIG. 7 is a front view of finger flange bracket 30 of FIG. 1. FIG. 8 is a sectional view taken on line 8—8 of FIG. 7 of finger flange bracket 30. FIG. 9 is a sectional view taken on line 9—9 of FIG. 7.

Finger flange bracket 30 includes a plurality of end slots, each for receiving and retaining a different size finger flange. Each end slot is comprised of a pair of forks. First slot 32 is dimensioned to receive and retain the finger flange for a 0.5 cc syringe. First slot 32 includes a front fork 33 dimensioned to span the syringe barrel and having back face 34 and a rear fork 35 dimensioned to span the syringe behind the finger flange and having a front face 36. Faces 34,36 are separated from one another to define the receiving slot 32 dimensioned to receive and retain the finger flange for a 0.5 cc syringe such that the finger flange bears against rear fork front face 36 as the syringe is filled.

Second slot 32' is dimensioned to receive and retain the finger flange for a 5 and a 10 cc syringe. Second slot 32' includes a front fork 33' dimensioned to span the syringe barrel and having back face 34' and a rear fork 35' dimensioned to span the syringe back of the finger flange and having a front face 36'. Faces 34',36' are separated from one another to define the receiving slot 32' dimensioned to receive and retain the finger flange for a 5 or 10 cc syringe such that the finger flange bears against rear fork front face 36' as the syringe is filled.

Preferably, finger flange bracket 30 is removably attachable to the remainder of arm 20 as to be able to change brackets to accommodate different size syringes. Finger flange bracket 30 includes means, such as prongs 38 having fastener holes 39, for removably retaining bracket 30 to the remainder of arm 20.

FIG. 10 is a front view of an alternate embodiment of finger flange bracket 30'. FIG. 11 is a section view taken on line 11—11 of FIG. 10. FIG. 12 is a section view taken on line 12—12 of FIG. 10. Alternate finger flange bracket 30' includes a slot 32" dimensioned to receive and retain the finger flange for a 3 cc syringe or similar syringe wherein barrel shield 88 comes nearly up to finger flange 85 and thumb flange 87 is close to finger guard 85 in the empty condition. With such syringes, the plunger flange receiving slot 52 and the finger flange receiving slot 32" are close together in the closed position and shield 88 must be able to approach finger flange slot 32" except for only the thickness of front fork 33". Slot 32" includes a front fork 33" dimensioned to span the syringe barrel and having back face 34" and a rear fork 35" dimensioned to span the syringe back of the finger flange and having a front face 36". Faces 34",36" are separated from one another to define the receiving slot 32" dimensioned to receive and retain the finger flange for a 3 cc syringe such that the finger flange bears against rear fork front face 36' as the syringe is filled. Prongs 38" having fastener holes 39" are used for removably attaching bracket 30' to the remainder of arm 20.

Second member distal arm distal end 44 terminates in thumb flange bracket means, such as thumb flange bracket 50, for receiving and retaining syringe thumb flange 87.

FIG. 4 is a front view of thumb flange bracket 50. FIG. 5 is a sectional view taken on line 5—5 of FIG. 4. FIG. 6 is a sectional view taken on line 6—6 of FIG. 4 of thumb flange bracket 50. Thumb flange bracket 50 includes a front fork 53 wherein the distance between the tines varies to span the syringe plunger shaft of a variety of syringes and such that the front fork back face 54 bears against the thumb flange front face as holder 10 is opened. A resilient backing plate 55 may be provided to form a slot 52 for insertion of thumb flange 87. Resilient backing plate 55 includes a front face 56 that may bear against the back of the thumb flange to more firmly hold thumb flange 87 and to push plunger back into barrel if necessary. Thumb flange bracket 50 may be removably attached to the remainder of arm 42 so that alternate configuration thumb flange brackets may easily be attached to accommodate syringes of uncommon dimension. Prongs 58 having fastener holes 59 are used for removably attaching bracket 50 to the remainder of arm 40.

Having described the invention, it can be seen that it provides a very convenient device for filling a syringe with radioactive fluid without exposing the worker to radiation. The holder accommodates different size syringes. The holder allows free maneuvering of syringe in relation to the vial. The detachable bracket design allows removable of contaminated brackets.

Although a particular embodiment of the invention has been illustrated and described, various changes may be made in the form, composition, construction, and arrangement of the parts without sacrificing any of its advantages. Therefore, it is to be understood that all matter herein is to be interpreted and illustrative and not in any limiting sense and it is intended to cover in the appended claims such modifications as come within the true spirit and scope of the invention.

I claim:
1. In combination:
   a syringe including:
      a barrel having a needle end and a back end; said barrel including:
         a finger flange on said barrel back end; said finger flange having a front side; and a back side; and
      a plunger having a front end slidingly engaged in said barrel and a back end; said plunger including:
         a thumb flange on said plunger back end; said thumb flange having a front side and a back side; and
   a holder for filling said syringe comprising:
      a first rigid elongate member comprising:
         a distal arm including:
            a hinge end; and
            a distal end terminating in finger flange bracket means for receiving and retaining said syringe finger flange; and
         a proximal arm including:
            a hinge end; and
            a proximal end;
      a second rigid elongate member having:
         a distal arm including:
            a hinge end; and
            a distal end terminating in thumb flange bracket means for receiving and retaining said syringe thumb flange; and
         a proximal arm including:
            hinge end; and
            a proximal end;
      hinge means hingedly connecting said first member to said second member at said hinge ends such that said first and second members pivot about said hinge from a closed position, wherein said distal ends are in close proximity for receiving said finger flange and said thumb flange of said syringe when said plunger is fully inserted in said barrel and wherein said proximal ends are separated, to an open position, wherein said distal ends are separated, by moving said proximal ends closer together.

2. The combination of claim 1 wherein:
said arm proximal ends each includes a finger loop.

3. The combination of claim 1 wherein:
said finger flange bracket means includes:
   a front fork having a back face; said front fork adapted to span said barrel such that said finger flange bears against said front fork back face; and
   a rear fork having a front face; said rear fork adapted to span said syringe to the back of said finger flange such that said finger flange bears against said rear fork front face.

4. The combination of claim 1 wherein:
said thumb flange bracket means includes:
   a plunger fork having a back face; said plunger fork adapted to span said plunger such that said thumb flange bears against said fork back face.

5. The combination of claim 4 wherein:
said thumb flange bracket means further includes:
   a backing plate bearing against the back of said thumb flange.

6. The combination of claim 1 wherein:
said holder further includes:
   metering means for restricting the distance between first and second said elongate member distal ends in the open position.

7. The combination of claim 6 wherein:
said metering means includes:
   adjustment means for adjusting the restricted distance between said first and second elongate member distal ends in the open position.

8. A holder for filling a syringe of the type having: a barrel having a needle end and a back end; the barrel including a finger flange on the barrel back end; the finger flange having a front side and a back side; and a plunger having a front end slidingly engaged in the barrel and a back end; the plunger including a thumb flange on the plunger back end; the thumb flange having a front side and a back side; said holder comprising:
   a first rigid elongate member comprising:
      a distal arm including:
         a hinge end; and
         a distal end terminating in finger flange bracket means for receiving and retaining the syringe finger flange; said finger flange bracket means including:
            a front fork having a back face; said front fork adapted to span the barrel such that the finger flange bears against said front fork back face; and
            a rear fork having a front face; said rear fork adapted to span the syringe to the back of the finger flange such that the finger flange bears against said rear fork front face;
      a proximal arm including:
         a hinge end; and
         a proximal end;
   a second rigid elongate member having:
      a distal arm including:
         a hinge end; and
         a distal end terminating in thumb flange bracket means for receiving and retaining the syringe thumb flange; said thumb flange bracket means including:
            a plunger fork having a back face; said plunger fork adapted to span the plunger such that the thumb flange bears against said fork back face;
a proximal arm including:
hinge end; and
a proximal end;
hinge means hingedly connecting said first member to said second member at said hinge ends such that said first and second members pivot about said hinge from a closed position, wherein said distal ends are in close proximity for receiving the finger flange and the thumb flange of the syringe when the plunger is fully inserted in the barrel and wherein said proximal ends are separated, to an open position, wherein said distal ends are separated, by moving said proximal ends closer together.

9. The holder of claim 8 wherein:
said arm proximal ends each includes a finger loop.

10. The holder of claim 8 wherein:
said thumb flange bracket means further includes:
a backing plate bearing against the back of said thumb flange.

11. The holder of claim 8 further including:
overdraw protection means for restricting the distance between said first and second elongate member distal ends in the open position.

12. The holder of claim 11 wherein:
said overdraw protector includes:
adjustment means for adjusting the restricted distance between said first and second elongate member distal ends in the open position.

13. A holder for filling syringes of various sizes; the syringes of the type having: a barrel having a needle end and a back end; the barrel including a finger flange on the barrel back end; the finger flange having a front side and a back side; and a plunger having a front end slidingly engaged in the barrel and a back end; the plunger including a thumb flange on the plunger back end; the thumb flange having a front side and a back side; said holder comprising:
a first rigid elongate member comprising:
a distal arm including:
a hinge end; and
a distal end terminating in finger flange bracket means for receiving and retaining syringe finger flanges of a plurality of sizes;
a proximal arm including:
a hinge end; and
a proximal end;
a second rigid elongate member having:
a distal arm including:
a hinge end; and
a distal end terminating in thumb flange bracket means for receiving and retaining syringe thumb flanges of a plurality of sizes;
a proximal arm including:
a hinge end; and
a proximal end;
hinge means hingedly connecting said first member to said second member at said hinge ends such that said first and second members pivot about said hinge from a closed position, wherein said distal ends are in close proximity for receiving the finger flange and the thumb flange of the syringe when the plunger is fully inserted in the barrel and wherein said proximal ends are separated, to an open position, wherein said distal ends are separated, by moving said proximal ends closer together.

14. The holder of claim 13 wherein:
said finger flange bracket means includes:
a plurality of fork pairs; each fork pair for receiving and retaining a different size finger flange; each fork pair including:
a front fork having a back face; said front fork adapted to span the barrel such that the finger flange bears against said front fork back face; and
a rear fork having a front face; said rear fork adapted to span the syringe to the back of the finger flange such that the finger flange bears against said rear fork front face.

15. The holder of claim 13 wherein:
said thumb flange bracket means includes:
a plunger fork having a back face; said plunger fork adapted to span plungers of various widths such that the thumb flange bears against said fork back face.

16. The holder of claim 13 wherein:
said arm proximal ends each includes a finger loop.

17. The holder of claim 13 wherein:
said thumb flange bracket means further includes:
a backing plate bearing against the back of said thumb flange.

18. The holder of claim 13 further including:
metering means for restricting the distance between said first and second elongate member distal ends in the open position.

19. The holder of claim 18 wherein:
said metering means includes:
adjustment means for adjusting the restricted distance between said first and second elongate member distal ends in the open position.

* * * * *